US006416477B1

(12) United States Patent
Jago

(10) Patent No.: US 6,416,477 B1
(45) Date of Patent: Jul. 9, 2002

(54) ULTRASONIC DIAGNOSTIC SYSTEMS WITH SPATIAL COMPOUNDED PANORAMIC IMAGING

(75) Inventor: James R. Jago, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 6 days.

(21) Appl. No.: 09/644,193

(22) Filed: Aug. 22, 2000

(51) Int. Cl.$^7$ .................................................. A61B 8/00
(52) U.S. Cl. ........................................................ 600/447
(58) Field of Search ................................. 600/437, 443, 600/447; 128/916; 382/128

(56) References Cited

U.S. PATENT DOCUMENTS

| | | | |
|---|---|---|---|
| 4,070,905 A | 1/1978 | Kossoff | |
| 4,159,462 A | 6/1979 | Rocha et al. | |
| 4,233,988 A | 11/1980 | Dick et al. | |
| 4,649,327 A | 3/1987 | Ishii | |
| 4,649,927 A | 3/1987 | Fehr et al. | |
| 4,751,846 A | 6/1988 | Dousse | |
| 5,396,890 A | 3/1995 | Weng | |
| 5,453,575 A | 9/1995 | Haviland et al. | |
| 5,479,926 A | 1/1996 | Ustuner et al. | |
| 5,538,004 A | 7/1996 | Bamber | |
| 5,566,674 A | 10/1996 | Weng | |
| 5,575,286 A | 11/1996 | Weng et al. | |
| 5,655,535 A | 8/1997 | Friemel et al. | |
| 5,782,766 A | 7/1998 | Weng et al. | |
| 5,885,218 A | 3/1999 | Teo et al. | |
| 5,908,390 A | 6/1999 | Matsushima et al. | |
| 6,159,152 A | * 12/2000 | Sumanaweera et al. | 600/443 |
| 6,328,693 B1 | * 11/2001 | Miyatake et al. | 600/437 |
| 6,364,835 B1 | * 4/2002 | Hossack et al. | 600/443 |

FOREIGN PATENT DOCUMENTS

| | | |
|---|---|---|
| WO | WO 83 00993 | 3/1983 |
| WO | WO 98 24065 | 6/1998 |

OTHER PUBLICATIONS

Feigenbaum, Echocardiography, Lea & Febiger, 1976 at pp 32–34, Philadelphia, PA.
Carpenter et al., Technical Note—A Multimode Real Time Scanner, Ultrsound in Med. & Biol., vol. 6, pp 279–284, Pergamon Press Ltd. 1980, Great Britain.
Berson et al., Compound Scanning With a Electrically Steered Beam, Ultrasonic Imaging 3, pp 303–308, Academic Press, Inc. 1981.
Shattuck et al., Compound Scanning With a Phased Array, Ultrasonic Imaging 4, pp 93–107, Academic Press, Inc. 1982.
Jesperson et al., Multi–Angle Compound Imaging, Ultrasonic Imaging 20, pp 81–102, Dynamedia, Inc. 1998.

* cited by examiner

Primary Examiner—Francis J. Jaworski
(74) Attorney, Agent, or Firm—W. Brinton Yorks, Jr.

(57) ABSTRACT

A method and apparatus are described which produce spatially compounded panoramic ultrasonic images by electronically steering beams in a plurality of different look directions as a transducer is moved in relation to a panoramic image field. The received echo information is compounded, then aligned and combined with previously acquired echo information to form a spatially compounded panoramic image. Alternatively, the received echo information may be aligned with previously acquired echo information, then combined to produce spatial compounding and a panoramic image in one process.

41 Claims, 11 Drawing Sheets

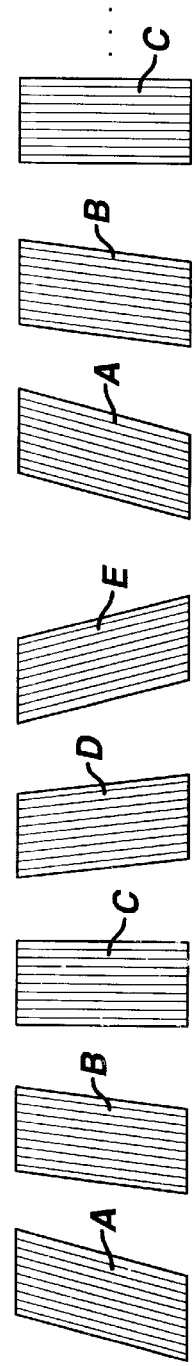
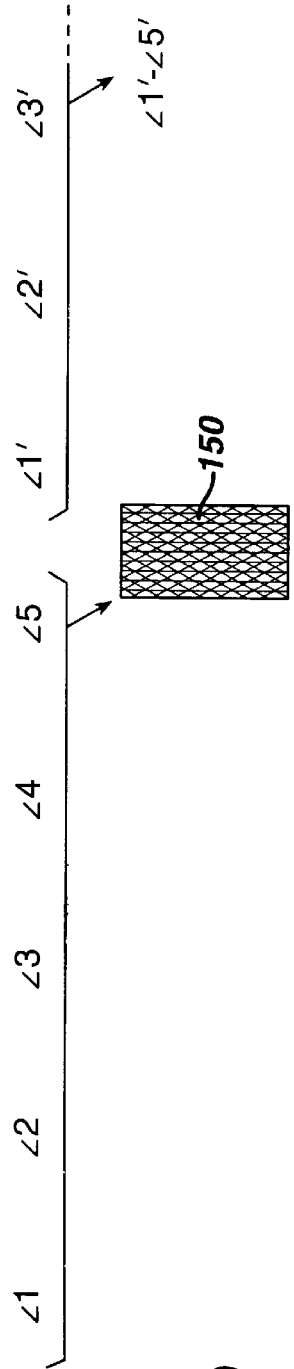
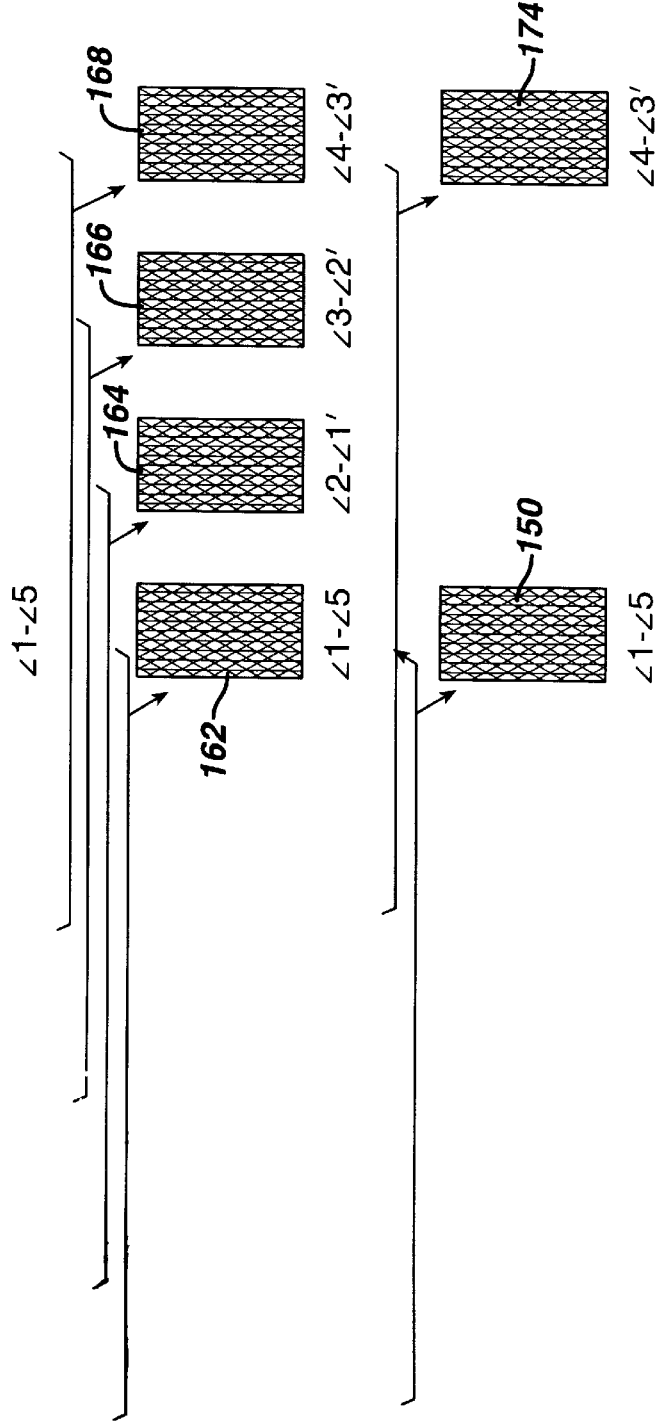
FIG. 7a
FIG. 7b
FIG. 7c
FIG. 7d

ULTRASONIC DIAGNOSTIC SYSTEMS WITH SPATIAL COMPOUNDED PANORAMIC IMAGING

This invention relates to ultrasonic diagnostic imaging systems and, in particular, to ultrasonic diagnostic imaging systems which produce spatially compounded panoramic images.

A method of processing and displaying ultrasonic images which is presently commercially available is known as extended field of view or panoramic imaging. In a basic realtime imaging mode, an ultrasonic transducer produces realtime images of the area of the body immediately in front of the transducer aperture. When the transducer is moved to another location on the body, the images will be of the area in front of the transducer aperture at the new location. That is, as the transducer is moved along the body, the ultrasound system will continuously produce an image of the area currently in front of the transducer aperture at any given moment. Panoramic imaging produces a composite image covering all of the areas which were in front of the transducer aperture including its starting and ending locations and every location in between. Panoramic imaging was initially performed over twenty years ago by B-arm ultrasound scanners, which would send and receive scanlines as the transducer was moved. The spatial location of each scanline was tracked by position sensors in the B-arm and the scanlines then assembled to form a continuous image under the path of travel of the transducer. In today's commercial systems the transducer used is an array transducer which continuously scans and acquires image frames. The need for the B-arm is obviated by correlating successive image frames on the basis of their common (overlapping) image content. When the array transducer is moved in a path such that successive image frames are overlapping and are co-planar there is generally sufficient correlation to align the image frames to each other. The aligned image frames are assembled together to form a continuous image of the tissue under the path of travel of the transducer. Panoramic images are produced in this manner by the methods and apparatus described in U.S. Pat. No. 5,782,766, for instance.

U.S. Pat. No. 5,538,004 shows another ultrasound display technique which utilizes frame to frame alignment. In this patent each new realtime image is aligned with a preceding one, then rotated as needed so that the viewer is always seeing the anatomy in the image from the same spatial reference, even as the transducer views the pathology from different orientations. The result is an image stabilizing effect. The author of the '004 patent recognizes that the image alignment process could be used in other image improvement procedures such as compounding. In U.S. Pat. No. 5,566,674 this extension is made by acquiring images of the same anatomy in the body from different transducer positions as demonstrated in FIG. 1 of that patent. The images are aligned, then compounded to form a new image with reduced shadowing and speckle.

It is desirable to have an imaging technique which combines all of the favorable attributes of the above systems, that is, a panoramic image in which shadowing and speckle are reduced by compounding. The technique suggested by the '004 and '674 patents, acquiring images from different transducer positions, has numerous drawbacks, however. Many paths along which a transducer is moved for panoramic imaging are substantially linear, such as the leg when imaging the saphenous veins. While points in the image may be interrogated by different scanlines of the image frame from frame to frame, the apertures of the two scanlines are usually highly correlated and produce little if any compounding effect because the scanlines in the overlapping image areas are substantially parallel. In other areas of the body such as the abdomen, the torso is generally too large with too much attenuation to be able to view the same anatomy from both sides of the body. Thus the diversity in views of the anatomy needed for compounding often cannot be obtained by simply moving the transducer. Even if they can, the transducer displacement required to acquire them, the distortion caused by tissue deformation from the transducer, and the possibility that the two views will not be co-planar and hence not correlated all increase the likelihood that the panoramic imaging registration algorithm will fail. It is desirable to be able to produce spatially compounded panoramic images without these drawbacks.

In accordance with the principles of the present invention, spatially compounded panoramic ultrasound images are produced by acquiring images as an array transducer is translated in relation to an area to be scanned. As the transducer is moved scanlines are electronically steered in a plurality of look directions relative to the transducer. The electronically steered scanlines are combined to form spatially compounded images which are aligned and combined to form a spatially compounded panoramic image. In one embodiment spatially compounded images are initially formed, then aligned and combined to form the panoramic image. In another embodiment component image frames of different look directions are aligned and then combined to form the spatially compounded panoramic image in one combining step, which reduces blurring from the transducer motion. In the first approach, the spatially compounded images may be produced at the rate of once for each full sequence of look directions, once for each new look direction, or after a partial new sequence of look directions have been scanned.

In the drawings:

FIGS. 7a–7d illustrate different techniques for acquiring and combining component frames from different look directions to form spatially compounded panoramic images in accordance with the principles of the present invention;

Figure 1:
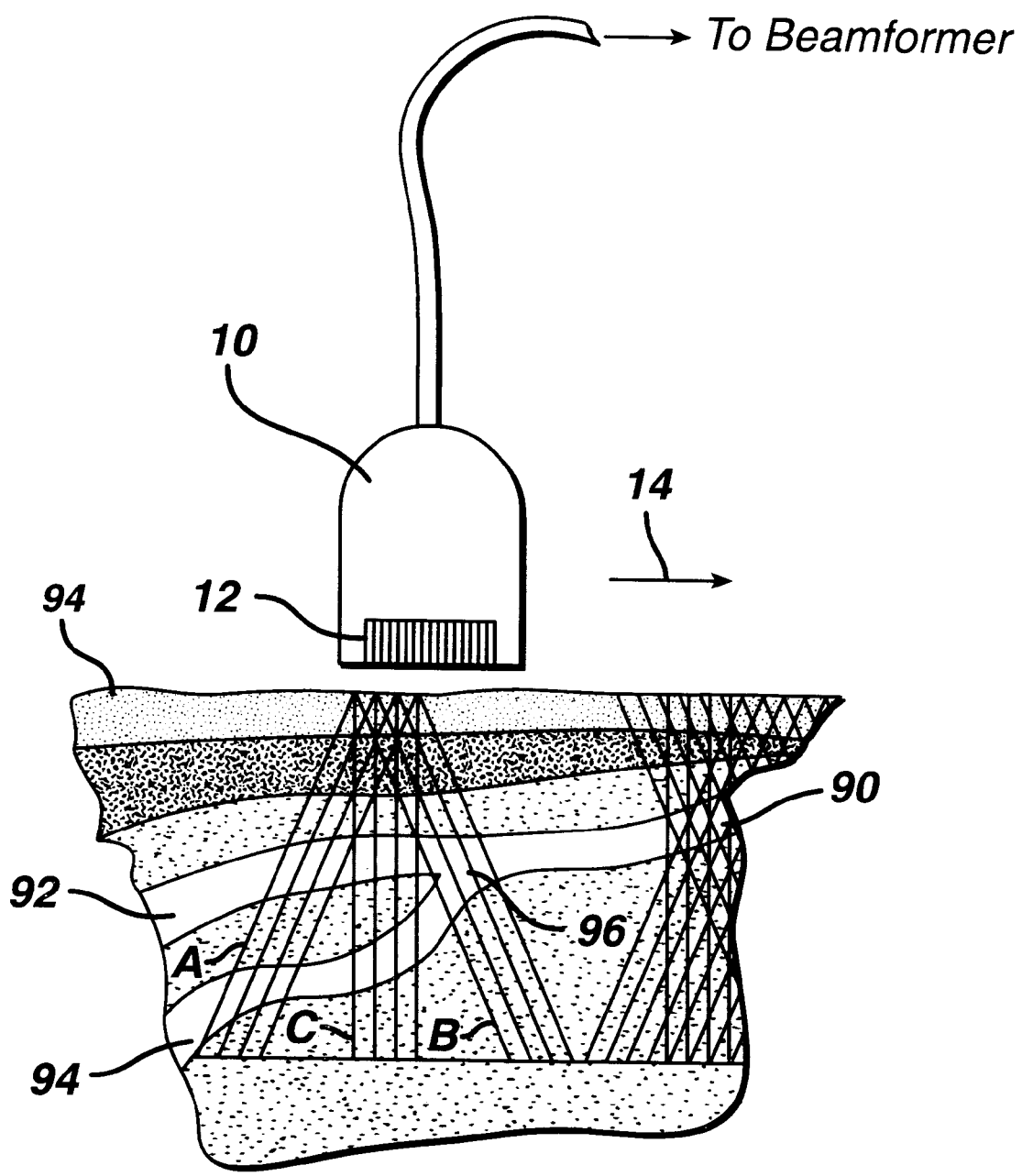
FIG. 1 illustrates the scanning of a spatially compounded panoramic image in accordance with the principles of the present invention.

FIG. 1 illustrates panoramic scanning in accordance with the present invention. A scanhead 10 is moved along the surface 94 of the body to produce a panoramic image of the tissue and vessels 92, 94, 96 beneath the path of travel of the scanhead. Generally an ultrasonic couplant (not shown) is applied between the scanhead and the skin surface to facilitate sliding the scanhead and the passage of ultrasound between the scanhead and the body. The scanhead includes an array transducer 12 and the scanhead is moved generally in line with the image plane of the transducer as indicated at 14 so that successive images will have some common image content. As the scanhead is translated the array transducer is operated to transmit and receive ultrasonic beams which are electronically steered in a plurality of look directions. FIG. 1 illustrates three beam steering directions by the scanlines indicated at A, B, and C. The scanlines at A are steered to the left, the scanlines at B are steered to the right, and the scanlines at C are steered straight ahead from the array transducer. While this example only shows three steering directions for clarity of illustration, in a constructed embodiment up to nine different steering directions are used. FIG. 1 illustrates the use of a steered linear array transducer, but a steered phased array transducer or steered curved array transducer as shown in U.S. patent [application Ser. No. 09/577,021] may also be used. The beam steering angles differ sufficiently so that points in the body which are interrogated by multiple beams are viewed at look directions differing sufficiently to give the improved image quality of spatial compounding when echoes from the point are combined. Transmission and reception of the differently steered beams may be interleaved in any order, but in a preferred embodiment component image frames of scanlines of the same steering direction are acquired in succession, as discussed below. As the scanhead is moved in the direction 14 shown in the drawing, the tissue and vessels beneath the scanhead are interrogated by overlapping scanlines of multiple look directions as shown at the right portion 90 of the drawing. Echoes from common points are combined to produce spatial compounding, and the scanlines beneath the path of travel of the scanhead are assembled in one image to produce a spatially compounded panoramic image.

An advantage of this scanning technique is that the tissue of interest is rapidly electronically scanned from multiple predetermined look directions so that the spatial compounding effect is reliably obtained. It will be appreciated that moving a linear array transducer without beam steering along a flat surface of the body, such as down the leg, will produce no spatial compounding effect as the points in the image will always be viewed from the same look direction. If the surface of the body along which the transducer is move is curved or irregular, some spatial compounding may occur, but the effect can be extremely variable as it will be a function of the irregularity of the path of travel and the distance over which the transducer is moved, and many areas of the image may exhibit no spatial compounding effect at all. Even the use of a curved array without beam steering can only produce a spatial compounding effect, if any, which is strongly a function of the distance moved by the transducer. Electronic beam steering can eliminate much of this variability, reliably producing a more uniform spatial compounding effect along the entire panoramic image. A further advantage is that the compounding of echoes from rapidly electronically steered look directions need not rely upon the accurate registration of component frames during panoramic image formation, which is often the limiting factor in using averaging for panoramic image combining because of the blurring caused by elemental image misregistration.

Figure 2:
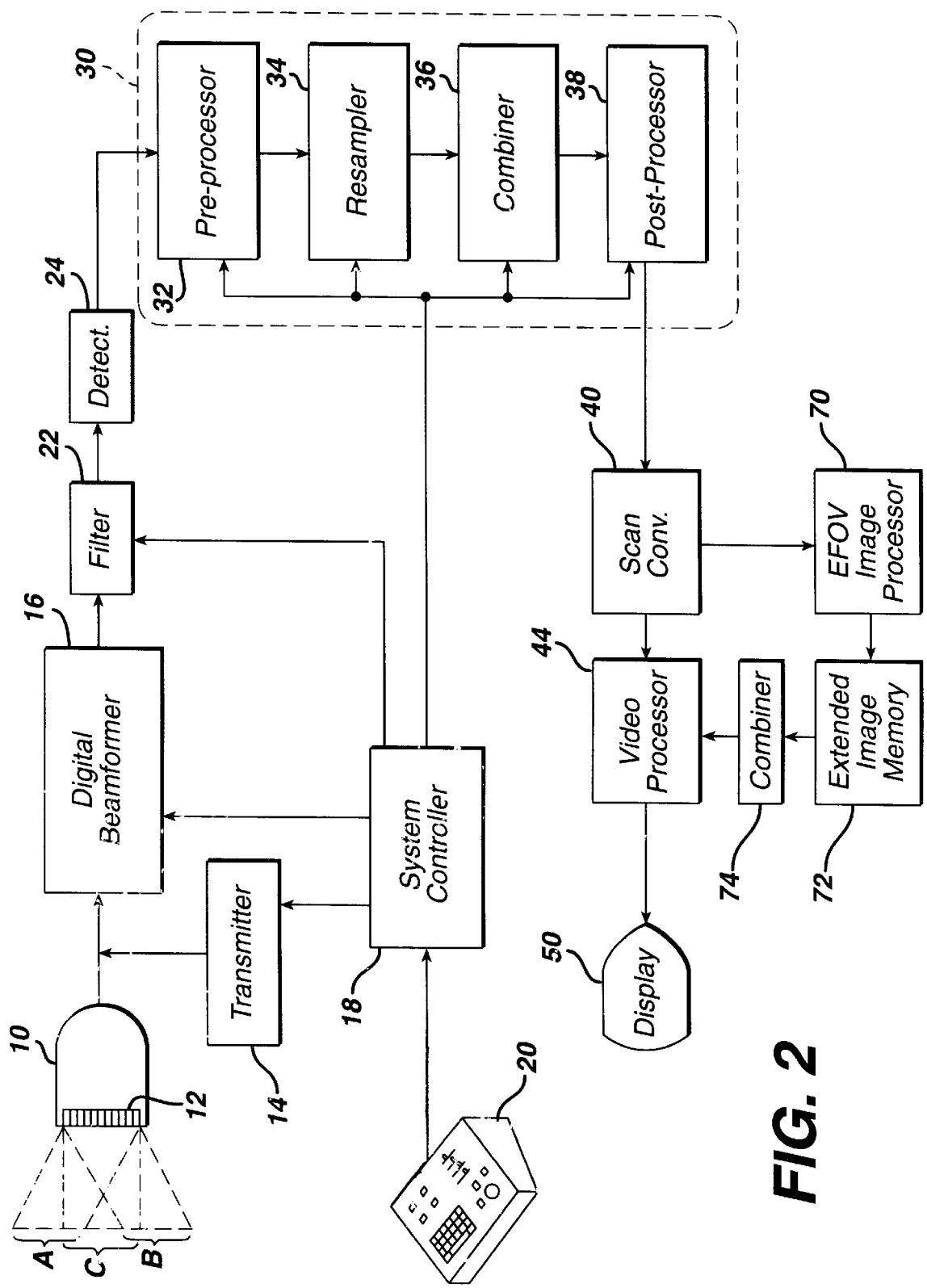
FIG. 2 illustrates in block diagram form an ultrasonic diagnostic imaging system constructed in accordance with the principles of the present invention.

Referring to FIG. 2, an ultrasonic diagnostic imaging system constructed in accordance with the principles of the present invention is shown. A scanhead 10 including an array transducer 12 transmits beams at different angles over an image field denoted by the dashed rectangle and parallelograms. Three groups of scanlines are indicated in the drawing, labeled A, B, and C with each group being steered at a different angle relative to the scanhead. The transmission of the beams is controlled by a transmitter 14 which controls the phasing and time of actuation of each of the elements of the array transducer so as to transmit each beam from a predetermined origin along the array and at a predetermined angle. The echoes returned from along each scanline are received by the elements of the array, digitized by analog to digital conversion, and coupled to a digital beamformer 16. The digital beamformer delays and sums the echoes from the array elements to form a sequence of focused, coherent digital echo samples along each scanline. The transmitter 14 and beamformer 16 are operated under control of a system controller 18, which in turn is responsive to the settings of controls on a user interface 20 operated by the user of the ultrasound system. The system controller controls the transmitter to transmit the desired number of scanline groups at the desired angles, transmit energies and frequencies. The system controller also controls the digital beamformer to properly delay and combine the received echo signals for the apertures and image depths used.

The scanline echo signals are filtered by a programmable digital filter 22, which defines the band of frequencies of interest. When imaging harmonic contrast agents or performing tissue harmonic imaging the passband of the filter 22 is set to pass harmonics of the transmit band. The filtered signals are then detected by a detector 24. In a preferred embodiment the filter and detector include multiple filters and detectors so that the received signals may be separated into multiple passbands, individually detected and recombined to reduce image speckle by frequency compounding. For B mode imaging the detector 24 will perform amplitude detection of the echo signal envelope. For Doppler imaging ensembles of echoes are detected and assembled for each point in the image and are Doppler processed to estimate the Doppler shift or Doppler power intensity.

In accordance with the principles of the present invention the digital echo signals are processed by spatial compounding in a processor 30. The digital echo signals are initially pre-processed by a preprocessor 32. The pre-processor 32 can preweight the signal samples if desired with a weighting factor. The samples can be preweighted with a weighting factor that is a function of the number of component frames used to form a particular compound image. The pre-processor can also weight edge lines that are at the edge of one overlapping image so as to smooth the transitions where the number of samples or images which are compounded changes. The pre-processed signal samples may then undergo a resampling in a resampler 34. The resampler 34 can spatially realign the estimates of one component frame or to the pixels of the display space. This may be desirable when there is motion between image frames, there is motion within an image, or there is scanhead motion during image acquisition. However, in many of the embodiments described below, this realignment is bypassed and is performed by the panoramic image processor when elemental images are aligned to form the panoramic image.

After resampling the image frames are compounded by a combiner 36. Combining may comprise summation, averaging, peak detection, or other combinational means. The samples being combined may also be weighted prior to combining in this step of the process. Finally, post-processing is performed by a post-processor 38. The post-processor normalizes the combined values to a display range of values. Post-processing can be most easily implemented by look-up tables and can simultaneously perform compression and mapping of the range of compounded values to a range of values suitable for display of the compounded image.

The compounding process may be performed in estimate data space or in display pixel space. The compound images may be stored in memory (not shown) in either estimate or display pixel form. If stored in estimate form the images may be scan converted by scan converter 40 when replayed from the memory for display. The scan converter and memory may also be used to render three dimensional presentations of the spatially compounded images as described in U.S. Pat. Nos. 5,485,842 and 5,860,924. Following scan conversion the spatially compounded images are processed for display by a video processor 44 and displayed on an image display 50.

In accordance with the principles of the present invention the spatially compounded image data is used to form a panoramic image. The image data is coupled to an EFOV image processor 70. The EFOV image processor, which may operate with either estimate data (pre-scan converted) images or display data (scan converted pixel data) images, receives each newly acquired image during the panoramic mode of operation and computes the displacement and rotation between the new image and a previously acquired elemental image of the panoramic image, as more fully described below. The EFOV image processor stores the new image in registration with the previously acquired elemental images in an extended image memory 72 as described below. Each time the panoramic image is extended by the addition of new image data, the EFOV image data stored in the extended image memory 72 is extracted from the memory and combined by a combiner 74 to form a new panoramic image, which is coupled to the video processor 44 for viewing on the display 50.

Figure 3:
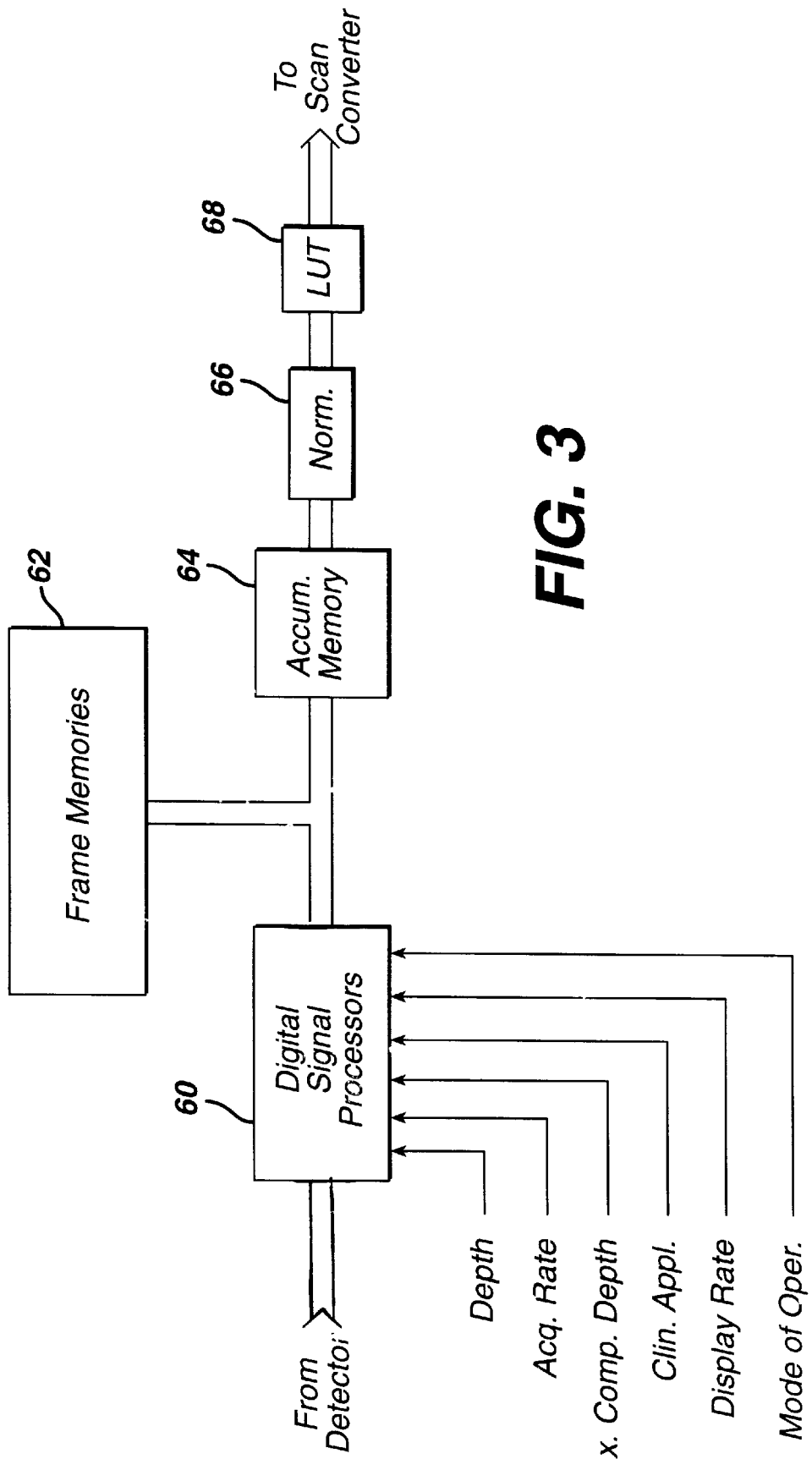
FIG. 3 illustrates in block diagram form a preferred implementation of the spatial compounding processor of FIG. 2.

FIG. 3 illustrates a preferred implementation of the spatial compounding processor 30 of FIG. 2. The processor 30 is preferably implemented by a general purpose microprocessor or CPU, or one or more digital signal processors 60 which process the image data in various ways. The processor 60 can weight the received image data and can resample the image data to spatially align pixels from component frame to component frame, for instance. The processor 60 directs the processed image frames to a plurality of frame memories 62 which buffer the individual image frames. The number of image frames capable of being stored by the frame memories 62 is preferably at least equal to the maximum number of image frames to be compounded such as sixteen frames. Preferably the processor is responsive to control parameters including image display depth, depth of region of greatest compounding, clinical application, compound display rate, mode of operation, scanhead motion and acquisition rate for determining the number of images to compound at a given instant in time. The processor selects component frames stored in the frame memories 62 for assembly as a compound image in accumulator memory 64. Various embodiments of the accumulator memory which subtract the oldest component frame when adding a new component frame, or which accumulate different compound images simultaneously, are described in U.S. Pat. No. 6,126,599, the contents of which are incorporated herein by reference. The compounded image formed in the accumulator memory 64 is weighted or mapped by a normalization circuit 66, then compressed to the desired number of display bits and, if desired, remapped by a lookup table (LUT) 68. The fully processed compounded image is then transmitted to the scan converter for formatting and display as an elemental image of a panoramic image.

Figure 4B:
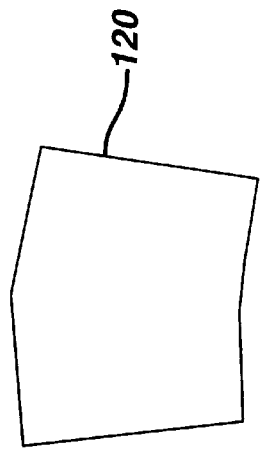
FIGS. 4a and 4b illustrate three overlapping elemental images which form a panoramic image.
Figure 4A:
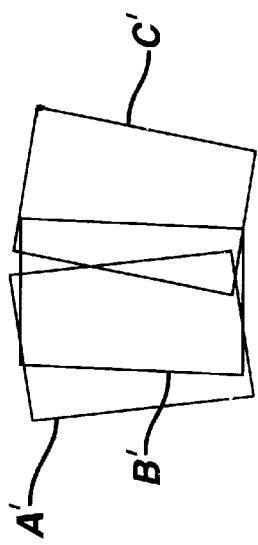
Figure 5:
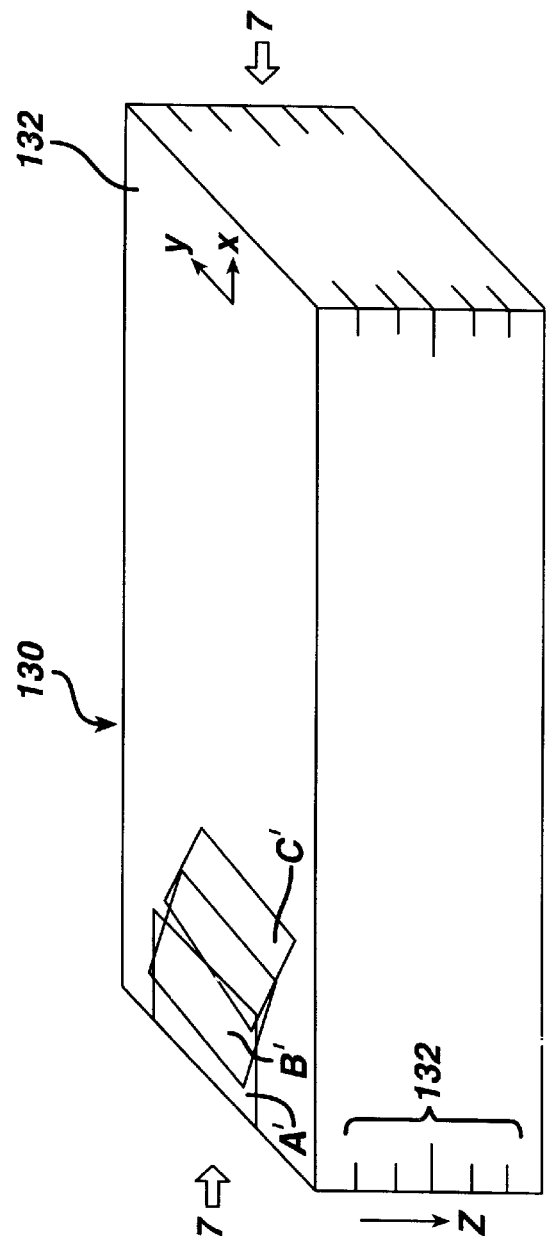
FIG. 5 depicts the organization of a panoramic image history buffer.

The EFOV image processor 70 receives elemental images from the spatial compounding processor 30 such as the sequence of partially overlapping elemental images A', B', and C' shown in FIG. 4a. The processor 70 computes the displacement from one elemental image to the next on the basis of their overlapping (common) image areas. The registration algorithms for computing this displacement are well known, including block matching, correlation, normalized correlation, sum of absolute or squared differences, gradient descent or mutual information techniques. Alternatively sensors of the motion or displacement of the scanhead can be used to sense the registration parameters, including Doppler sensing. When the displacement necessary to align (register) a new elemental image to a previous elemental image in a panoramic image is known, the new elemental image can be combined with the others to produce an extended image. The overlapping regions of the elemental images are combined by techniques such as averaging, median filtering, peak detection, or other linear, non-linear or adaptive processes. One way to do this is to employ a buffer memory as the extended image memory 72 in which a single panoramic image formed from previously acquired elemental images is stored. The new elemental image is then added to the panoramic image in the buffer, generally through some form of weighting or averaging, to produce a new panoramic image for display. Once the new elemental image has been added to the panoramic image it can no longer be separately identified, as it is blended into and becomes an integral part of the panoramic image. In a preferred embodiment of the present invention, a history buffer is used for the extended image memory 72, in which the pixels of the individual elemental images continue to be separately distinguishable. FIG. 5 depicts the organization of a preferred history buffer 130. The x,y coordinates of the history buffer 130 shown on the top surface 132 correspond to the maximum sight area of a displayed panoramic image. The column depth z of the history buffer is the maximum number of pixels of different elemental images which can be stored and combined to form each pixel of the panoramic image. In the illustrated embodiment the history buffer is shown to be six pixels deep as shown by delineations 132. In a constructed embodiment the history buffer may be eight to sixteen pixels deep.

Figure 6A:
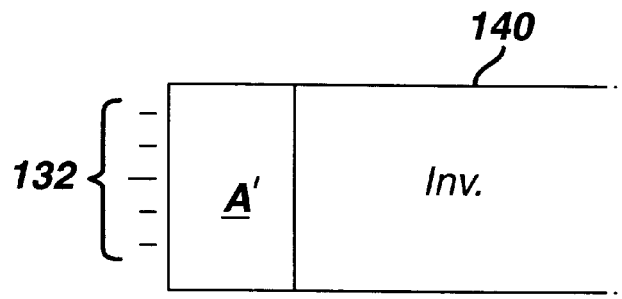
FIGS. 6a–6c illustrate how successive elemental images are entered into the history buffer of FIG. 5.
Figure 6B:
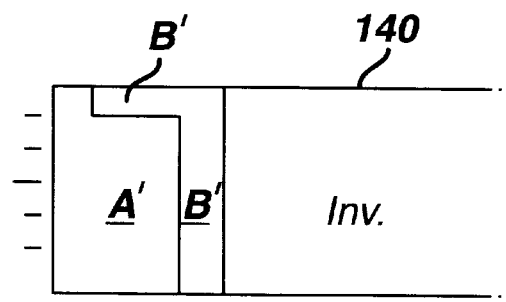
Figure 6C:
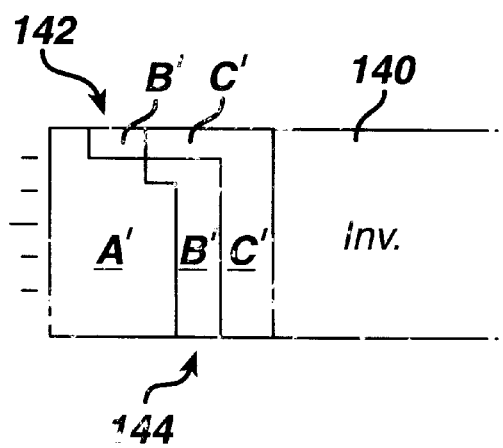

Referring back to FIG. 4a, three exemplary elemental images A', B', and C' are shown which are acquired as the initial elemental images for a panoramic image. Image A' is the first to be acquired as the scanhead moves from left to right to acquire images A', B', and C' in succession. Image A' is therefore entered first into the history buffer 130 and is aligned to the left edge of the buffer as shown in FIG. 5. If the scanhead were moving from right to left, the first image A' would be aligned at the right side of the buffer so that the panoramic image could be extended from right to left instead of from left to right as depicted in this example. When the image A' is entered into the history buffer, it completely fills the pixel storage areas (depth z) beneath its x,y coordinates with image A' pixel values as shown in FIG. 6a. FIGS. 6a–6c depict the history buffer cross-section in a plane 140 between arrows 7—7 in FIG. 5. The remaining pixel storage areas of the history buffer continue to be set to invalid values at this time.

Image B' is next acquired and aligned with image A' as described above. Image B' is stored in the history buffer in its aligned position in x,y coordinates with respect to image A'. Where image B' overlays image A', the image A' pixels are "pushed down" by one pixel depth so that the upper pixel is occupied by pixel B' and the remaining are still occupied by image A' pixel values, as shown in FIG. 6b. In areas where image B' does not overlay image A', the full pixel depth is filled with image B' pixel values.

When image C' is acquired and aligned with image B' the push down process is repeated as shown in FIG. 6c. In the columns indicated by arrow 142 where all three images overlap, the top pixel is from image C', the next pixel down is from pixel B', and the remaining pixel depth is filled with image A' pixels. In image areas where only images B' and C' overlap, the top pixel in the column is an image C' pixel, and those below are image B' pixels.

This process continues as additional elemental images are acquired to extend the panoramic image. The finite depth of the history buffer, six pixels in this example, limits the number of images which can overlap at any pixel location to the most recent six overlapping images. Older image pixels at the location are "pushed out" of the bottom of the buffer which, in the z direction, operates as a FIFO (first in, first out) buffer. This is unlike the above-described technique of simply recursively adding a new elemental image to a panoramic image, where an unlimited number of overlapping images are blended together. The finite limit of the history buffer provides a benefit of reduced image blurring as compared to the technique of simply recursively blending a panoramic image, since very old images in the history buffer overlay are removed by the FIFO push-down process. This is not possible where elemental images are blended into the panoramic image and are no longer separately distinguishable, unless each elemental image is stored and its position tracked for subsequent subtraction from the panoramic image. In addition the history buffer readily permits the scanning direction to be reversed during a scan. Another benefit is that the algorithm for combining elemental images into a panoramic image can be changed and different algorithms applied to the same extended image set.

Each time a new elemental image is added to the history buffer the combining algorithm is applied to the pixel data by combiner 74 to form a pixel of a panoramic image from each column of pixels in the history buffer. It is seen that the initial filling of an entire column with pixels of the first image acquired at an x,y coordinate effects a weighting of the pixel data in favor of the initial image. If such weighting is not desired, the columns in the history buffer could only be filled one pixel depth at a time, or by another desired depth weighting. The combining algorithm may effect a summing of the pixel data at each column, an averaging or median filtering process, or some other linear or nonlinear filtering function (FIR, IIR, static, conditional, or adaptive) automatically or adaptively selected or chosen by the user. The panoramic image for elemental images A', B', and C' would appear as shown by outline 120 in FIG. 4b. In a preferred embodiment the area of the most recently acquired image, all or some (e.g., the leading edge) of the area currently beneath the transducer aperture, is displayed as a live, realtime image, which assists the user when moving the scanhead along a selected path of anatomy. The previously acquired portion of the panoramic image is generally displayed as a static image, although it can also be displayed in motion when acquired and displayed in a synchronized manner as with the assistance of a heart gate (ECG signal).

FIGS. 7a–7d illustrate different techniques for combining component frames from different look directions to form spatially compounded panoramic images. FIG. 7a illustrates an acquisition sequence of five component frames acquired from different steering directions. The first component frame A is acquired with the scanlines all steered in a look direction $\angle 1$, the second component frame B is acquired with the scanlines all steered in a look direction $\angle 2$, the third component frame C is acquired with the scanlines all steered in a look direction $\angle 3$, the fourth component frame D is acquired with the scanlines all steered in a look direction $\angle 4$, and the fifth component frame E is acquired with the scanlines all steered in a look direction $\angle 5$. The sequence then repeats with another component frame A steered in a look direction $\angle 1'$, another component frame B steered in a look direction $\angle 2'$, another component frame C steered in a look direction $\angle 3'$, and so on. One way to spatially compound this acquisition sequence is to wait until a complete new sequence of five component frames is acquired and then combine them, as shown in FIG. 7b. Component frames A–E are combined to form one spatially compounded image 150 which is a combination of look directions $\angle 1$–$\angle 5$. After a new sequence of component frames A–E is acquired they are combined to form a second spatially compounded image (not shown) which is a new combination of look directions $\angle 1'$–$\angle 5'$. An advantage of this technique is that each spatially compounded image which is used as an elemental image for a panoramic image is formed from entirely different image data. A disadvantage of this technique is that the frame rate at which a new elemental image is added to the panoramic image is limited in proportion to the number of component frames of a spatially compounded image and the time required to acquire them, which can give a discontinuous appearance to the buildup of the panoramic image.

FIG. 7c illustrates a second compounding technique which provides elemental images for the panoramic image at a more rapid rate. In this sequence spatially compounded image 162 combines the first five acquired component frame of look directions $\angle 1$–$\angle 5$. When another component frame is acquired a second spatially compounded image 164 is formed of look directions $\angle 2$–$\angle 1'$. Spatially compounded image 166 is formed of look directions $\angle 3$–$\angle 2'$, and spatially compounded image 168 is formed of look directions $\angle 4$–$\angle 3'$. Spatially compounded elemental images for panoramic imaging are thus produced at the component frame acquisition rate, with each elemental image including four-fifths of the image data as the preceding elemental image. The buildup of the panoramic image will appear much smoother and more continuous as elemental images are added to the panoramic image at a rapid rate. This compounding technique may be carried out by the methods and apparatus described in the aforementioned U.S. Pat. No. 6,126,599, including an image accumulator memory from which the oldest component frame is subtracted and the new component frame added, or by the use of multiple image accumulator memories which simultaneously produce compounded images of different sets of component frames. is formed of look directions $\angle 3$–$\angle 2'$, and spatially compounded image 168 is formed of look directions $\angle 4$–$\angle 3'$. Spatially compounded elemental images for panoramic imaging are thus produced at the component frame acquisition rate, with each elemental image including four-fifths of the image data as the preceding elemental image. The buildup of the panoramic image will appear much smoother and more continuous as elemental images are added to the panoramic image at a rapid rate. This compounding technique may be carried out by the methods and apparatus described in the aforementioned U.S. patent [application Ser. No. 09/335,159], including an image accumulator memory from which the oldest component frame is subtracted and the new component frame added, or by the use of multiple image accumulator memories which simultaneously produce compounded images of different sets of component frames.

Figure 8:
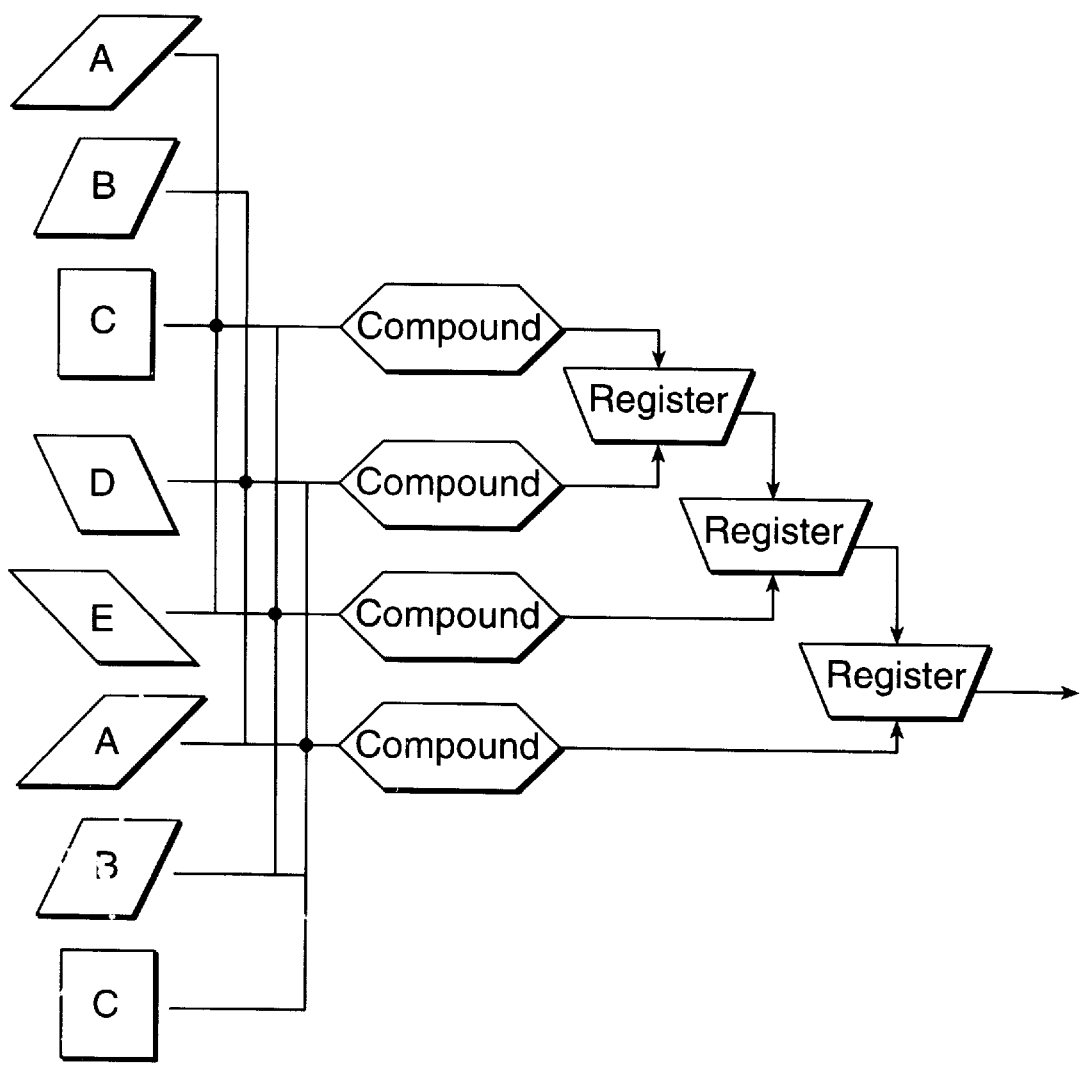
FIG. 8 illustrates a process for compounding and registering component frames acquired as shown in FIG. 7c.

The technique of FIG. 7c is used in the spatially compounded panoramic imaging process diagrammed in FIG. 8. The component frames representing a complete acquisition sequence (one set of all angles A–E in this example) are first combined before registration into a compounded image by the Compound process. This assumes that the scanhead movement during this sequence is negligible, otherwise the compound image will be blurred. In this example no component-frame-to-component-frame registration is performed by the compound image processor. This Compound process is repeated for every sequence of steered frames, ideally at the acquisition frame rate by for example an accumulator method described above. The sequence of compounded images formed as the scanhead is moved are then processed by the registration algorithm "Register" of the EFOV image processor 70 to generate a single panoramic image of compounded data. This approach has the advantage that the artifact reduction resulting from the spatial compounding should help the registration algorithm to be very robust. Also, the real-time component at the leading edge of the panoramic image already represents a compounded image without the need for further processing.

FIG. 7d illustrates a compounding technique which is intermediate the techniques of FIGS. 7b and 7c. This technique produces spatially compounded elemental images for panoramic imaging at a faster rate than FIG. 7b, reducing the discontinuous buildup appearance of that technique, but at a lesser rate than FIG. 7c, which reduces computational complexity. In FIG. 7d a spatially compounded image 172 is formed of look directions $\angle 1$–$\angle 5$. The next spatially compounded image 174 is formed after a plurality of new look directions are acquired and is formed of look directions $\angle 4$–$\angle 3'$. Each spatially compounded image contains some of the same image data as the preceding spatially compounded image, and includes a plurality of new look directions (in this example, three) so that the panoramic image process is not processing a large amount of redundant image data. The interval at which new spatially compounded images are produced in the technique of FIG. 7d is user variable; for instance, if the number of look directions is nine, the user might elect to have new spatially compounded images produced every four or five component frames. If the number of look directions is only three, the user may prefer to produce a spatially compounded image every three frames, the technique of FIG. 7b.

Figure 9:
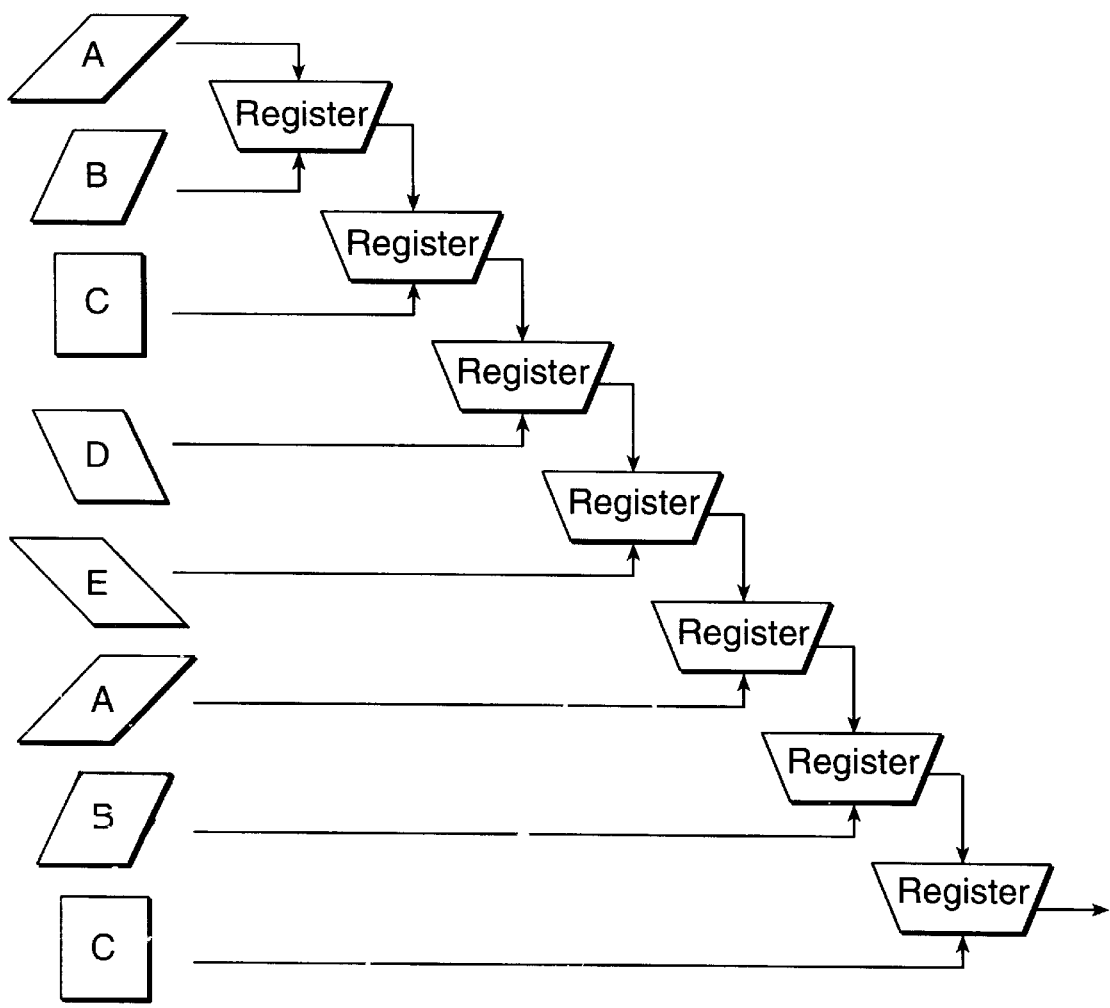
FIG. 9 illustrates a process for registering and combining component frames directly into a spatially compounded panoramic image.

FIG. 9 illustrates a spatially compounded panoramic imaging process in which steered component frames A–E can be input directly into the registration algorithm "Register" before they are combined, thus generating a panoramic image with significant spatial compounding even when scanning along a flat surface. In this process a single registration step registers component frames of different look directions directly into a panoramic image to produce the panoramic image and spatial compounding simultaneously. Note that the panoramic image itself is generated by continually registering each new component frame with the previous set of registered component frames, traceable back to the first frame A of the acquisition. Conversely, the real-time component of the panoramic image would be continuously updated by registering the N previous frames (where N is the number of unique steering angles) with the most recent frame.

Figure 10:
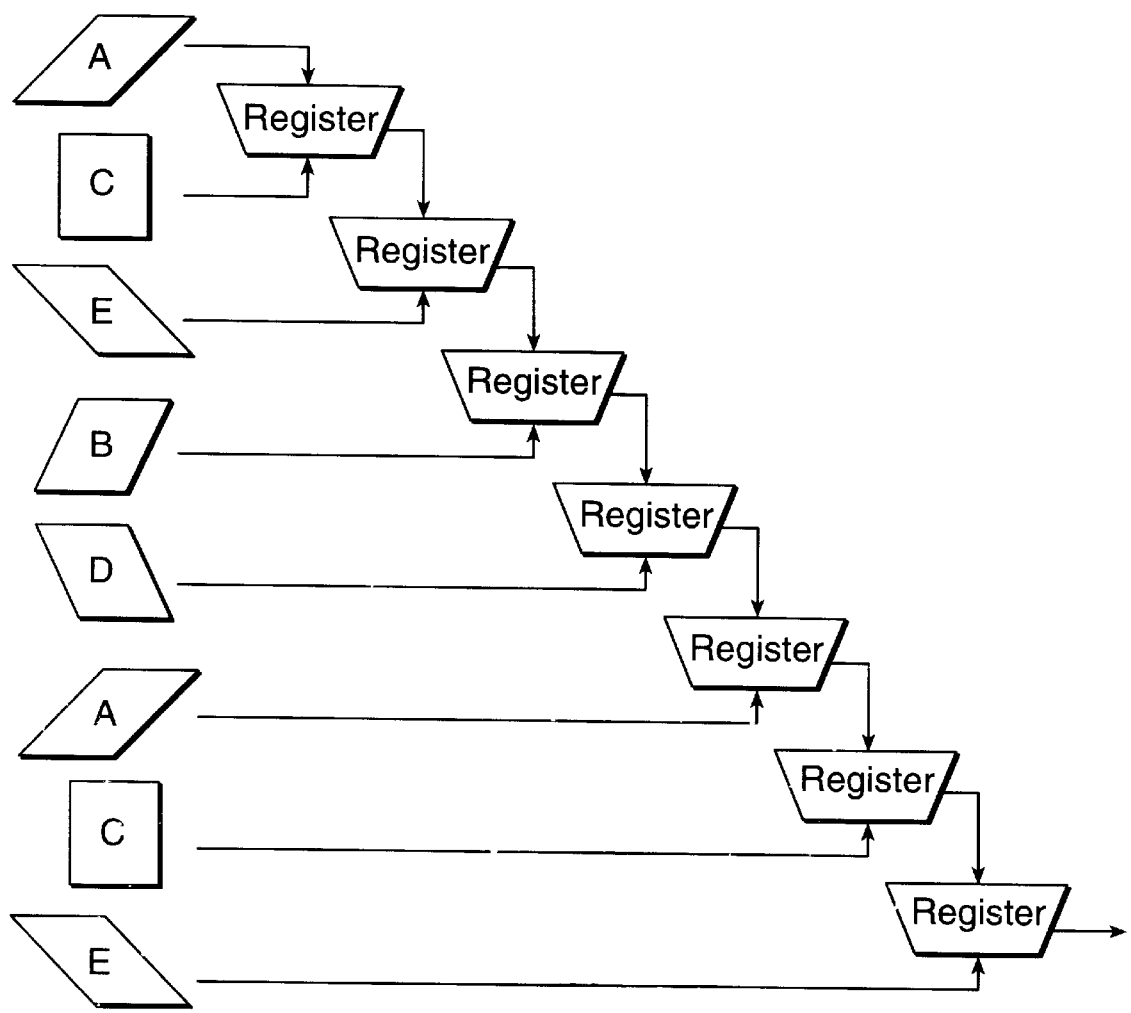
FIG. 10 illustrates a process for acquiring component frames of differing look directions which reduces the maximum steering angle difference between successive component frames.

One potential disadvantage of this method is that most algorithms for determining the frame-frame registration become less reliable when there is a large difference in view angle between the frames. This is mainly because of the influence of ultrasound image artifacts, such as anisotropy, which can cause echoes and shadows from some targets to appear in different locations or at different intensities in images obtained from different angles. For the sequence shown in FIG. 9, the difference in view angle between frames is small except for the transitions between the end of one complete set of angles (frame E) and the beginning of the next (frame A'). An alternative acquisition sequence is shown in FIG. 10, which maintains a more uniform (and lesser maximum) angle difference between all frames at the expense of a higher minimum angle difference. Other angle sequences will have different advantages and disadvantages in registration robustness and beam steering programming.

Figure 11:
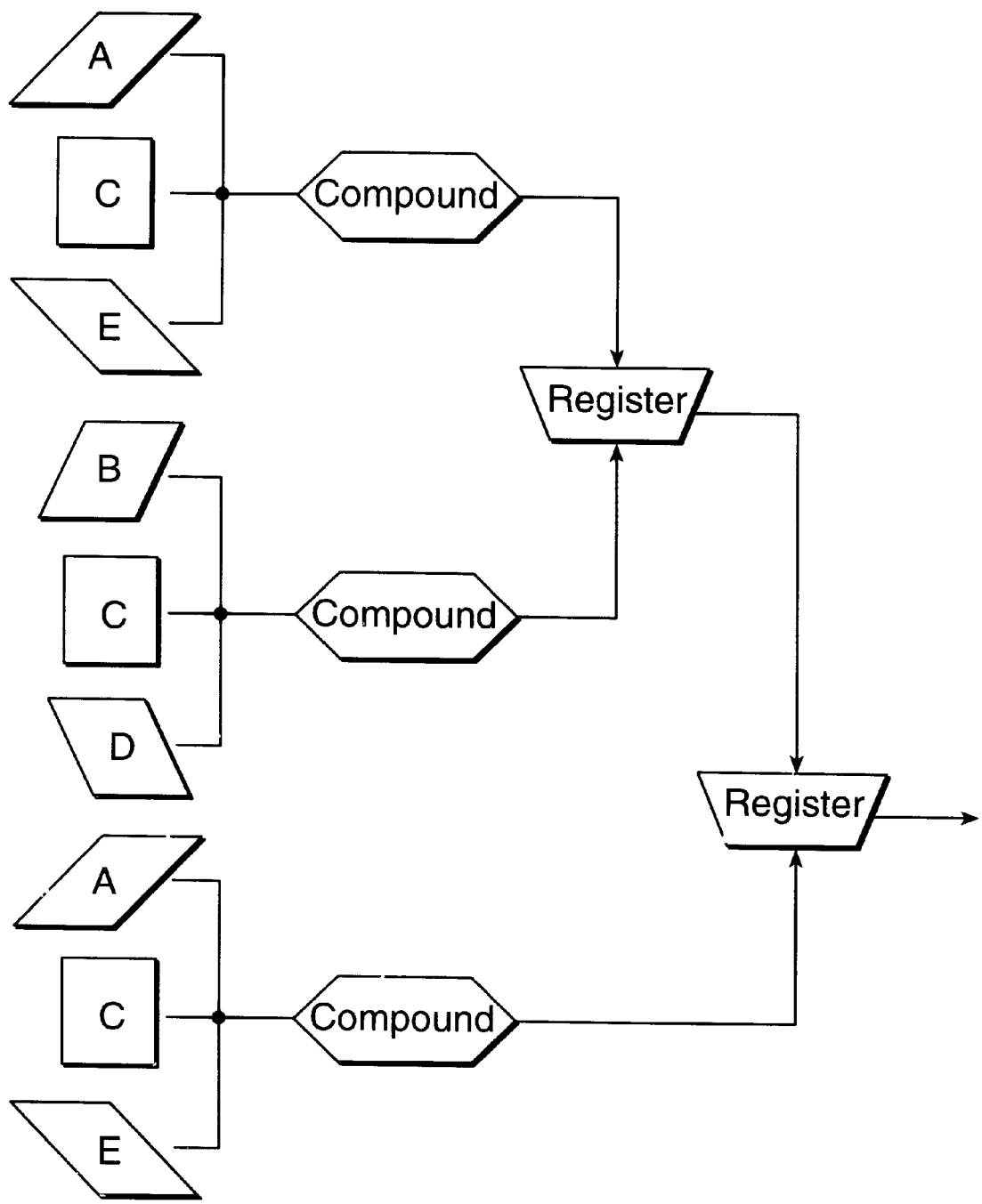
FIG. 11 illustrates a spatially compounded panoramic imaging process in which partially compounded images are used.

FIG. 11 illustrates a spatially compounded panoramic imaging process that is a compromise between the processes shown in FIGS. 9 and 10 above. This process compounds a sub-set of steered component frames (three of the five, in this example) to produce a first partially compounded image (e.g., A,C,E), followed by compounding of the remaining set of steered frames (e.g., B,C,D) to produce a second partially compounded image. In the illustrated steering sequence, a non-steered frame C is acquired for every sub-sequence to ensure that the real-time (i.e., most recent image data) component of the panoramic image always includes non-steered data. This process would be repeated continuously, with the partially compounded images (A,C,E and B,C,D) being input sequentially into the registration algorithm Register. This approach would allow some reduction of image artifacts and hence improvement in the robustness of the registration, while not incurring as much motion blurring during rapid scanhead movement as for the process of FIG. 8.

Figure 12:
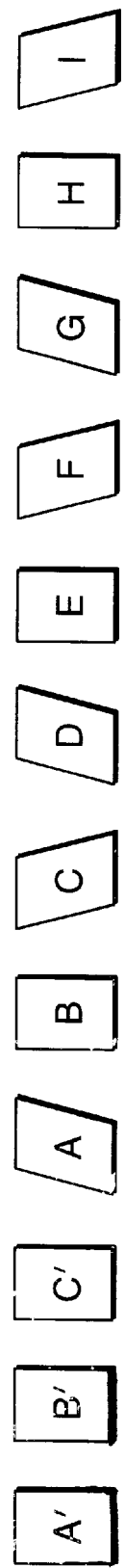
FIG. 12 illustrates a sequence of frames in which the registration algorithm only operates on frames of the same steering direction.

In an embodiment of the present invention it is desirable to register component frames for spatial compounding and elemental images of a panoramic image as accurately as possible. This ability is made more difficult when component frames exhibiting different steering directions are being registered because, as mentioned above, a target can return different echoes when interrogated from different angles, which puts great demand on the registration algorithm. FIG. 12 illustrates a technique which addresses this problem by registering only component frames of a common steering direction. FIG. 12 illustrates a sequence of component frames A, B, C, etc. which are acquired as the transducer is moved along the body. Each component frame is acquired after translation of the transducer and its image to a new location. It may be seen that the translation between frames A and D is a combination of the translations from frame A to frame B to frame C to frame D. This may be expressed mathematically as $$A \rightarrow D = A \rightarrow B + B \rightarrow C + C \rightarrow D$$

The translations between other frames of a common look direction may similarly be expressed as $$B \rightarrow E = B \rightarrow C + C \rightarrow D + D \rightarrow E$$

$$C \rightarrow F = C \rightarrow D + D \rightarrow E + E \rightarrow F$$

$$D \rightarrow G = D \rightarrow E + E \rightarrow F + F \rightarrow G$$

and so on. The translation between the frames on the left side of each equation are computed by the registration algorithm of the panoramic image processor, as each pair of frames is acquired at the same look direction, easing the demands put on the registration algorithm. The translation between succesively acquired frames is then computed from the simultaneous equations. For example, the translations C→F and D→G are computed by the registration algorithm. The translation between successively acquired frames F→G is calculated from $$D{\rightarrow}G\text{-}C{\rightarrow}F{=}D{\rightarrow}E{+}E{\rightarrow}F{+}F{\rightarrow}G\text{-}C{\rightarrow}D\text{-}D{\rightarrow}E\text{-}E{\rightarrow}F$$

$$D{\rightarrow}G\text{-}C{\rightarrow}F{=}F{\rightarrow}G\text{-}C{\rightarrow}D$$

$$F{\rightarrow}G{=}C{\rightarrow}D{+}D{\rightarrow}G\text{-}C{\rightarrow}F$$

With D→G and C→F being determined by the registration algorithm and C→D being determined from a previous equation, the translation from frame F to frame G can be determined from the last equation. Thus, the registration algorithm is only called upon to determine the translation between commonly steered frames, with the frame-to-frame displacement between successively acquired frames of differing steering directions determined from the simultaneous equations.

In order to start the above process, the translation between two pairs of successively acquired frames must be known, A→B and B→C. Once these interframe displacements are known, the others can all be determined by registering frames of common look directions and use of the simultaneous equations. Thus, at the outset of the process, the registration algorithm can be called upon to determine the translation between frames of different look directions, in this example, from A to B and from B to C. A variation of this which eases the task of the registration algorithm is for the user to pause momentarily before beginning to move the transducer in order to allow the transducer to acquire at least one full sequence of frames of the different look directions while the transducer is at rest. The frame to frame translations between these frames will thus be zero, and consequently the initial equations will have some frame to frame translation values of zero. Once the transducer begins to move, the nonzero values will be determined by measuring the translation between frames of the same steering direction and the process will proceed as described above.

As a third alternative, these translations may be approximated by starting with three precursor frames A', B' and C' as shown in FIG. 12, which are acquired at the same look direction. The translations from A' to B' and from B' to C' are determined by the registration algorithm using these commonly steered frames, then used as the translations from A to B and from B to C. Given a substantially constant rate of transducer motion and high frame acquisition rate, the use of the translations between the precursor frames for those of the first frames in the sequence will be substantially accurate. The use of a sequence of commonly steered frames may be repeated during the acquisition process to estimate accumulated translation errors or make adjustments to the registration process as desired.

One skilled in the art will recognize that the foregoing discussion illustrates frame to frame translation computations simply with plus and minus signs, but that in a constructed embodiment in which frame to frame motion includes translation and rotation, the acutal computations may involve more complex matrix operations.

The technique of FIG. 12 is most accurate when only a few look directions are used for compounding, that is, when the sequence of component frames is relatively short. In the example of FIG. 12, the sequence of component frames is only three frames in duration. This is because the technique relies upon the capability of aligning commonly steered frames between which there may be substantial transducer translation and hence little common image content with which to register the two frames, putting the registration algorithm to a demanding task. Hence it may be desirable to activate this technique adaptively when the number of differently steered component frames is small, and to change to a different technique, such as simply trying to register successive frames, when the number of differently steered frames is high, e.g., eight or nine frames.

The frames which are registered in the foregoing examples may be entire image frames, or partial image frames, or image frames of reduced resolution or line density, or may be reference scanlines transmitted between displayed image frames for registration purposes as described in U.S. Pat. No. 6,117,081.

The final choice of which method to use in a particular case will depend on the speed of movement of the probe (and/or target), which could be clinical application dependent, and the inherent robustness of the chosen panoramic image registration algorithm to angle dependent artifacts. In general, the accuracy required to register component frames for spatial compounding is more demanding than the registration required to form a panoramic image from elemental images. Thus, when the probe is being moved slowly, it is usually preferable to spatially compound before panoramic image registration. When the probe is being moved quickly, which can produce a blurred spatially compounded image, it is usually preferable to send component frames directly to the panoramic image registration process and let the panoramic registration algorithm reduce blurring to the best of its capability. In a preferred embodiment this choice is made adaptively by detecting the degree of scanhead motion as described in U.S. Pat. No. 6,126,598 and automatically adjusting the spatial compounding and/or panoramic registration processes in response thereto. The panoramic imaging registration and combining algorithms may also be varied adaptively in response to the degree of scanhead motion, as may the variables of spatial compounding as described in U.S. Pat. No. 6,210,328.

What is claimed is:

1. A method of producing a spatially compounded ultrasonic panoramic image comprising:

receiving echo information in an array transducer aperture located at a plurality of locations with respect to an image field from ultrasonic beams electronically steered in a plurality of look directions;

scanning the array to acquire echo information from a field of view which is greater than that of the transducer aperture;

spatially aligning the echo information;

combining spatially aligned echoes from points in the image field which have been interrogated from multiple look directions to produce a spatially compounded panoramic image which is greater than the transducer aperture.

2. The method of claim 1, wherein the combining comprises:

combining echoes from points in the image field which have been interrogated from multiple look directions to produce a spatially compounded image; and combining the spatially compounded image with a spatially compounded image acquired from a different aperture location to produce a spatially compounded panoramic image which is greater than the transducer aperture.

3. The method of claim 2, further comprising, prior to the last-named combining, aligning the first-named spatially compounded image with the spatially compounded image acquired from a different aperture location.

4. The method of claim 1, wherein the combining comprises extending a panoramic image by combining echoes from points which have been interrogated from multiple look directions to produce a spatial compounding effect at the points.

5. A method of producing a spatially compounded ultrasonic panoramic image comprising:

transmitting a plurality of electronically steered beams in a plurality of directions from an array transducer aperture as the transducer aperture is moved in relation to an extended image field so as to interrogate points in the extended image field from multiple look directions;

receiving echoes in response to the transmitting;

locationally organizing the received echoes; and combining locationally aligned echoes to produce a panoramic, spatially compounded ultrasonic image which is larger than the transducer aperture.

6. The method of claim 5, wherein combining comprises:

combining echoes from points in the image field which have been interrogated from multiple look directions to produce a spatially compounded image; and combining the spatially compounded image with a previously acquired spatially compounded image to produce a panoramic, spatially compounded ultrasonic image which is larger than the transducer aperture.

7. The method of claim 6, further comprising, prior to the last-named combining, aligning the first-named spatially compounded image with the previously acquired spatially compounded image.

8. The method of claim 5, wherein locationally organizing further comprises locationally aligning echo data which has not been spatially compounded with panoramic image data which has been spatially compounded.

9. The method of claim 8, wherein the combining simultaneously produces a spatial compounding effect and extends a panoramic image.

10. A method of producing a spatially compounded ultrasonic panoramic image comprising:

receiving, from a translating transducer aperture, sequences of component image frames, different component image frames of a sequence exhibiting scanlines electronically steered in a different look direction;

combining a plurality of the component image frames to produce an elemental spatially compounded image; and combining the elemental spatially compounded image with a previously acquired elemental spatially compounded image to produce a spatially compounded ultrasonic panoramic image.

11. The method of claim 10, wherein the first-named combining comprises combining a plurality of component image frames on a spatially aligned basis.

12. The method of claim 11, wherein the second-named combining further comprises aligning the elemental spatially compounded image with a previously acquired elemental spatially compounded image.

13. The method of claim 12, wherein aligning utilizes one of block matching, normalized correlation, correlation, sum of absolute differences, sum of squared differences, gradient descent, mutual information processing, Doppler sensing, or position or motion sensors.

14. The method of claim 10, wherein the first-named combining produces an elemental spatially compounded image for each received component image frame.

15. The method of claim 10, wherein the first-named combining produces an elemental spatially compounded image for each sequence of component image frames.

16. The method of claim 10, wherein the first-named combining produces an elemental spatially compounded image which includes a plurality of component image frames not included in a previous elemental spatially compounded image.

17. The method of claim 16, wherein the plurality of component image frames not included in a previous elemental spatially compounded image is less than the number of component image frames in a complete sequence of component image frames.

18. A method of producing a spatially compounded ultrasonic panoramic image comprising:

receiving, from a translating transducer aperture, a sequence of component image frames exhibiting scanlines electronically steered in a plurality of different look directions;

registering each component image frame with one or more registered component image frames; and combining the registered component image frames to produce a spatially compounded ultrasonic panoramic image.

19. The method of claim 18, further comprising the sequence in which component image frames are registered so that component image frames of the maximum steering direction diversity are not successively registered.

20. A method of producing a spatially compounded ultrasonic panoramic image comprising:

receiving, from a translating transducer aperture, sequences of component image frames, different component image frames of a sequence exhibiting scanlines electronically steered in a different look direction;

combining pluralities of component image frames which are a subset of the component image frames of a full sequence to produce a plurality of elemental spatially compounded images;

registering the elemental spatially compounded images; and combining the registered elemental spatially compounded images to produce a spatially compounded ultrasonic panoramic image.

21. The method of claim 20, wherein each subset includes a component image frame with scanlines steered normal to the transducer aperture.

22. An ultrasonic imaging system which produces a spatially compounded panoramic image comprising:

an array transducer;

a transmit controller, coupled to the array transducer, and operable to cause the array transducer to transmit beams electronically steered in a plurality of look directions as the array transducer is translated with respect to an image field;

a beamformer, coupled to the array transducer, which produces coherent echo signals in response to beams transmitted in a plurality of look directions;

a registration processor which aligns echo signals received from common points in an image field; and a combiner which combines aligned echo signals to produce spatially compounded panoramic image data.

23. The ultrasonic imaging system of claim 22, further comprising:

a spatial compounding processor, responsive to the echo signals produced by the beamformer, which produces spatially compounded echo signals;

wherein the registration processor and the combiner operate upon spatially compounded echo signals.

24. The ultrasonic imaging system of claim 22, wherein the transmit controller is operable to cause the array transducer to transmit beams for component images, wherein different component images exhibit beams steered in different look directions.

25. The ultrasonic imaging system of claim 24, further comprising:

a spatial compounding processor, responsive to component images exhibiting different look directions, which combines component images to produce elemental spatially compounded images;

wherein the registration processor and the combiner operate upon elemental spatially compounded images.

26. The ultrasonic imaging system of claim 25, wherein the spatial compounding processor includes an image memory from which a previous component image may be subtracted and a new component image added.

27. The ultrasonic imaging system of claim 25, wherein the spatial compounding processor includes a plurality of image memories which simultaneously assemble component images for different spatially compounded images.

28. The ultrasonic imaging system of claim 24, wherein said registration processor aligns a component image with one or more previously aligned component images.

29. The ultrasonic imaging system of claim 22, further comprising a history buffer, coupled to the registration processor and the combiner, which stores aligned echo signals.

30. The ultrasonic imaging system of claim 29, wherein the history buffer is capable of storing only a finite number of echo signals for a particular pixel location.

31. A method of producing a spatially compounded ultrasonic panoramic image comprising:

receiving, from a translating transducer aperture, sequences of component image frames, different component image frames of a sequence exhibiting scanlines electronically steered in a different look direction;

registering component image frames which exhibit a common look direction;

registering component image frames which exhibit different look directions through use of the registered component image frames which exhibit a common look direction; and combining the registered component image frames to produce a spatially compounded ultrasonic panoramic image.

32. The method of claim 31, wherein a sequence of component image frames exhibits a sequence of look directions which is substantially the same as that of the preceding sequence of component image frames.

33. The method of claim 31, wherein registering component image frames which exhibit different look directions utilizes simultaneous equations.

34. The method of claim 33, wherein registering component image frames which exhibit a common look direction produces a measure of translation between the component image frames, wherein the measure of translation is used in the simultaneous equations.

35. The method of claim 34, wherein the simultaneous equations further use a computed translation between component image frames which exhibit different look directions.

36. The method of claim 31, wherein component image frames which exhibit a common look direction are registered by a registration algorithm; and wherein component image frames which exhibit different look directions are registered by computations utilizing registration data of component image frames which exhibit a common look direction.

37. The method of claim 36, wherein the computations further utilize computed registration data of component image frames which exhibit different look directions.

38. The method of claim 36, further comprising receiving, from the translating transducer aperture, a sequence of component image frames exhibiting scanlines electronically steered in a common look direction.

39. The method of claim 31, wherein the registering of component image frames which exhibit a common look direction registers frames which are non-sequential; and wherein the registering of component image frames which exhibit different look directions registers frames which are sequential.

40. The method of claim 39, wherein the registering of component image frames which exhibit a common look direction utilizes a registration algorithm which registers frames on the basis of their image information to determine a frame to frame translation factor; and wherein the registering of component image frames which exhibit different look directions registers frames by computing a frame to frame translation factor using a translation factor of the registration algorithm.

41. The method of claim 40, wherein the registering of component image frames which exhibit different look directions registers frames by computing a frame to frame translation factor further utilizes a computed frame to frame translation factor.

* * * * *

UNITED STATES PATENT AND TRADEMARK OFFICE
CERTIFICATE OF CORRECTION

PATENT NO. : 6,416,477 B1
DATED : July 9, 2002
INVENTOR(S) : James R. Jago et al.

It is certified that error appears in the above-identified patent and that said Letters Patent is hereby corrected as shown below:

<u>Title page,</u>
Item [75], should read:

-- [75] James R. Jago, Seattle;
      Lars Jonas Olsson, Woodinville;
      Robert E. Entrekin, Kirkland, all of WA (US) --

Signed and Sealed this

Twenty-ninth Day of October, 2002

*Attest:*

*Attesting Officer*

JAMES E. ROGAN
*Director of the United States Patent and Trademark Office*